United States Patent [19]

Kimoto et al.

[11] Patent Number: 5,207,507
[45] Date of Patent: May 4, 1993

[54] METHOD FOR CONTINUOUS THERMOGRAVIMETRIC ANALYSIS OF COAL

[75] Inventors: Hiroshi Kimoto, Sakai; Mikindo Saiga, Ikoma; Sekio Uemura, Kishiwada; Shoji Seike; Yoshihiko Ishida, both of Nagoya; Toshihiko Nakagawa, Hekinan, all of Japan

[73] Assignees: The Kansai Electric Power Co., Ltd.; NGK Insulators, Ltd., both of Japan

[21] Appl. No.: 848,680

[22] Filed: Mar. 9, 1992

[30] Foreign Application Priority Data

Mar. 15, 1991 [JP] Japan .................................. 3-76830

[51] Int. Cl.$^5$ .................... G01N 25/00; G01N 5/00
[52] U.S. Cl. ...................................................... 374/14
[58] Field of Search .......................................... 374/14

[56] References Cited

U.S. PATENT DOCUMENTS 4,388,410  6/1983  Arroyo et al. ........................ 374/14
4,838,705  6/1989  Byers, Jr. et al. .................... 374/14

FOREIGN PATENT DOCUMENTS 2-31131  2/1990  Japan .

OTHER PUBLICATIONS

Hodgson, A., "A comprehensive thermal analysis apparatus," J. Sci. Instrum., 40(2), pp. 61–65 (Feb. 1963).
Wiedemann, H., "Universal Measuring Instrument for Gravimetric Investigations under Variable Conditions," Mettler Instrument Corporation, Princeton, N.J. (Feb. 1969).
"Thermal Analysis in Corrosive Gas Atmospheres," Mettler Instrument Corporation, Bulletin T-103, Princeton, N.J. (Mar. 1967).

Primary Examiner—William A. Cuchlinski, Jr.
Assistant Examiner—Diego F. F. Gutierrez
Attorney, Agent, or Firm—Parkhurst, Wendel & Rossi

[57] ABSTRACT

A method for continuous thermogravimetric analysis of coal, or other materials rich in carbon, for volatile matter and ash content, including the steps of exposing a coal sample to an atmosphere consisting essentially of about 1 to 5% by volume of oxygen and the remainder being nitrogen and inevitable impurities at a first specified temperature for a first given time, weighing the coal sample to determine a first weight loss during the first given time, the first weight loss corresponding to the amount of volatile matter in the coal sample, burning the coal sample under an oxygen atmosphere having a higher than normal oxygen concentration for a second given time at a temperature sufficient to burn carbon containing materials in the coal sample, and weighing the coal sample to determine a second weight loss during the first given time and the second given time, the second weight loss corresponding to the amount of volatile matter and the amount of ash content in the coal sample.

9 Claims, No Drawings

METHOD FOR CONTINUOUS THERMOGRAVIMETRIC ANALYSIS OF COAL

BACKGROUND OF THE INVENTION AND DESCRIPTION OF THE PRIOR ART

This invention relates to a method for thermogravimetric analysis of coal due to the formation of volatile matters and ash contents.

When coal is used as a fuel, for example in a fire power plant, it is important to know thermal weight losses due to the formation of volatile matters and ash contents. For this purpose M 8812 in JIS specifies a standard method for thermogravimetric analysis of coal to give information on water, other volatile matters, and ash contents. According to the method in JIS, however, each analysis requires a distinct sample, and inevitably similar measurements have to be repeated; thus complete analysis takes a long time.

The method for thermogravimetric analysis to quantify volatile matters according to M 8812 in JIS, consists of: heating an electric furnace and adjusting temperatures of a specific space for a crucible inside the furnace uniformly to 900° C.; putting a sample (about 1 g) into a platinum crucible with a known weight; putting a lid on the crucible; tapping the bottom of the crucible on a clean, firm plane a few times to make the sample equal in depth inside the crucible; placing the crucible with the lid into the specific space under a nitrogen atmosphere in the uniform temperature in the furnace; heating the crucible under a nitrogen atmosphere in the furnace so that temperatures of the specific space in the furnace reach those in a range of 900°±20° C. within three minutes after placing the crucible; keeping the crucible under a nitrogen atmosphere in the furnace for seven minutes after placing the crucible into the specific space; taking the crucible out of the furnace; cooling the crucible on a cold metal plate for a minute; cooling the crucible in a desiccator; and measuring a weight of the crucible with the sample to obtain a relative weight loss of the sample.

The method for thermogravimetric analysis to quantify ash contents according to M 8812 in JIS, consists of: putting a sample (about 1 g) into a crucible with a known weight; placing the crucible into a furnace; heating the crucible under a normal atmosphere to 500° C. in about 60 minutes and then to 815° C. in about an additional 60 minutes or, if necessary, two to three hours; holding the crucible under a normal atmosphere in temperatures ranging from 805° C. to 825° C.; taking the crucible out of the furnace; cooling the crucible in a desiccator for twenty minutes; and measuring a weight of the crucible with the sample to obtain a relative weight loss of the sample.

To overcome the two independent time-consuming procedures, a method has been developed for continuous thermogravimetric analysis out of a single sample of coal. Japanese Patent Laid-Open No. 2-31131 (1990) has disclosed a method for thermogravimetric analysis, comprising: heating a first sample of coal in a crucible without a lid to 950° C. at a heating rate of 110° C. per minute under a nitrogen atmosphere to give a second sample; maintaining the second sample at 950° C. for three minutes to give a third sample; measuring a relative weight loss of the third sample; burning the third sample at 850° C. under an oxygen atmosphere; and measuring a second relative weight loss of the third sample. The values obtained in this method contain systematic errors compared to those obtained in the method in M 8812 in JIS, and, therefore, require corrections.

SUMMARY OF THE INVENTION

According to the present invention, there is provided a method for continuous thermogravimetric analysis of coal, comprising: heating a first sample of coal having a predetermined weight in a crucible to a first specified temperature under an essentially nitrogen atmosphere containing oxygen ranging from about 1 to about 5% by volume to give a second sample; maintaining the second sample at the first specified temperature under the essentially nitrogen atmosphere for a while to give a third sample; measuring a relative weight loss of the third sample; and burning the third sample at a second specified temperature, which will burn carbon containing materials in the sample, under an oxygen atmosphere while measuring weight changes of the third sample.

DESCRIPTION OF THE PREFERRED EMBODIMENT

The method according to the present invention enables continuous measurement of thermal weight losses due to formation of volatile matters and ash contents out of a single sample of coal, and the values for the losses obtained in this present method are in excellent agreement with those obtained in M 8812 in JIS without any correction. Though this method is suitably applied to coal of various types, other solid materials rich in carbon enjoy the benefits of the present invention.

We have studied the method to quantify volatile matters specified in M 8812 in JIS, and we have found that in the method in M 8812 in JIS a sample such as coal in a crucible undergoes slight oxidation in a combined process of heating a sample to 900° C. and maintaining it at about 900° C. to result in a slight weight loss.

In contrast, in the prior method disclosed a sample does not undergo oxidation as much as the method in M 8812 in the step of heating a sample to 950° C. and the following step of holding the sample at 950° C., because the sample is kept under a complete nitrogen atmosphere in these steps. Therefore, in the prior method the weight loss in a sample in these steps is much smaller than that in M 8812 in JIS, and this difference leads to systematic differences in values obtained between the two methods.

Therefore, in the step of heating a sample to a high enough temperature to decompose volatile matter in the coal sample, e.g., 950° C., and the following step of holding the sample at 950° C., in the method according to the present invention a sample is kept under an essentially nitrogen atmoshere containing oxygen ranging from 1% to 5% by volume, instead of being under a complete nitrogen atmosphere disclosed in the prior method. This small amount of oxygen in the atmosphere in the present invention allows a sample to undergo slight oxidation in the step of heating a sample to 950° C. and the following step of holding the sample at 950° C. in the same manner as the equivalent process in the method in M 8812 in JIS. Therefore, the method according to the present invention gives the values for relative weight losses that are in excellent agreement with those obtained by M 8812 in JIS without any corrections.

Moreover, according to the method in the present invention, even though measurements for relative weight losses are repeated for identical samples, the values obtained have satisfactory repeatability.

When a sample is kept under an essentially nitrogen atmosphere containing less than 1% oxygen in the step of heating a sample to 950° C. and the following step of holding the resultant sample for three minutes, the sample does not undergo sufficient oxidation, and the resultant values obtained for relative weight losses still contain systematic errors like those obtained in the prior method. Likewise, when a sample is kept under an essentially nitrogen atmosphere containing more than 5% oxygen in the step of heating a sample to 950° C. and the following step of standing the resultant sample for three minutes, the sample undergoes too much oxidation to give a value corresponding to more volatile matters than are actually present.

After measuring a weight loss due to volatile matters according to the present invention, measurements of a weight loss due to ash contents follow. First an essentially nitrogen atmosphere under which a sample is placed is changed into an oxygen atmosphere whose oxygen content is higher than a normal atmosphere. An atmosphere with an oxygen content over 99.5% by volume is favorable because the increased oxygen content helps combustion to shorten the analysis time required. An atmosphere with oxygen content higher than 99.9% is more favorable.

Then while a weight of a sample in the crucible was automatically measured every 30 seconds, combustible materials in the sample are burnt at 950° C. until the weight of the sample does not change any more. Typically it takes about 15 minutes to reach a constant weight, the second weight loss indicating the amount of volatile matter and the amount of ash content in the coal sample.

EXAMPLES

The present invention will now be described more in detail but it shall not be limited to the following examples.

Samples were prepared by atomizing Daido coal. Daido coal produced in the Daido area of Japan is one type of coal used in a fire power plant. Its heating value is 7000 cal/g, and its typical element analysis is: C, 75; H, 4; N, 1; S, 0.5. It contains 5.0% by weight of water, 30.7% by weight of volatile matters, and 7.9% by weight of ash contents. A thermobalance having a furnace on top with automatic temperature-measuring equipment was used for thermogravimetric analysis.

First the relative weight loss due to volatile matters was measured by the method in M 8812 in JIS to be 30.7%.

The standard procedure in the present invention is as follows: samples of coal powder were heated in crucibles without lids to 950° C. with a heating rate of 110° C. per minute under an essentially nitrogen atmosphere containing 0.1%, 1%, 5% and 10% by volume of oxygen. Each of the samples was maintained at 950° C. for three minutes. Then a relative weight loss of each sample due to volatile matters was automatically measured.

After changing the essentially nitrogen atmosphere into an oxygen atmosphere whose oxygen content was more than 99.5% by volume, crucible lids were removed and carbon-containing materials in each sample in a were burnt at 950° C. until the weight of the sample did not change any more while a weight of the crucible with the sample was automatically measured every 30 seconds. Typically it took about 15 minutes to reach a constant weight. For each oxygen concentration listed above, three runs were performed with identical samples.

The values obtained for the relative weight losses due to volatile matters are shown in the following table. When samples were kept under an essentially nitrogen atmosphere containing 1% and 5% by volume of oxygen in a step of heating the samples to 950° C. and the following step of holding the sample at 950° C., the relative errors of the values for the relative weight losses due to volatile matters are less than about 1%.

In contrast, when samples were kept under an essentially nitrogen atmosphere containing oxygen outside of the range from about 1% to about 5% in a step of heating the samples to 950° C. and the following step of holding the sample at 950° C., the relative errors of the values for the relative weight losses due to volatile matters were too large, and they would require some corrections.

TABLE

| atmosphere nitrogen | oxygen | relative weight losses due to volatile matters | errors compared to JIS values |
|---|---|---|---|
| 99.9% | 0.1% | 29.0% | −5.5% |
| 99.0% | 1.0% | 30.3% | −1.3% |
| 95.0% | 5.0% | 31.0% | 0.9% |
| 90.0% | 10.0% | 33.6% | 9.4% |

What is claimed is:

1. A method for continuous thermogravimetric analysis of coal for volatile matter and ash content, said method comprising the steps of:
   exposing a predetermined known weight of coal sample to an atmosphere consisting essentially of about 1 to 5% by volume of oxygen and the remainder being nitrogen and inevitable impurities at a first specified temperature for a first given time;
   weighing the coal sample to determine a first weight loss during the first given time, said first weight loss corresponding to the amount of volatile matter in the coal sample;
   buring the coal sample under an oxygen atmosphere having a higher than normal oxygen concentration for a second given time at a temperature sufficient to burn carbon containing materials in the coal sample; and
   weighing the coal sample to determine a second weight loss during the first given time and the second given time, said second weight loss corresponding to the amount of volatile matter and the amount of ash content in the coal sample.

2. The method of claim 1, wherein said first specified temperature is high enough to decompose volatile matter in the coal sample.

3. The method of claim 1, wherein said first specified temperature is about 950° C.

4. The method of claim 1, wherein said first given time is about three minutes.

5. The method of claim 1, wherein said second given time is about 15 minutes.

6. The method of claim 1, wherein said oxygen atmosphere contains oxygen in an amount of over 99.5% by volume.

7. The method of claim 6, wherein said oxygen atmosphere contains oxygen in an amount of at least 99.9% by volume.

8. A method for continuous thermogravimetric analysis of coal for volatile matter and ash content, said method comprising the steps of:

exposing a predetermined known weight of coal sample to an atmosphere consisting essentially of about 1 to 5% by volume of oxygen and the remainder being nitrogen and inevitable impurities at about 950° C. for a first given time of about three minutes;

weighing the coal sample to determine a first weight loss during the first given time, said first weight loss corresponding to the amount of volatile matter in the coal sample;

burning the coal sample under an oxygen atmosphere having a higher than normal oxygen concentration for a second given time at a temperature sufficient to burn carbon containing materials in the coal sample; and weighing the coal sample to determine a second weight loss during the first given time and the second given time, said second weight loss corresponding to the amount of volatile matter and the amount of ash content in the coal sample.

9. The method of claim 8, wherein said second given time is about 15 minutes.

* * * * *